United States Patent
Motoyama et al.

[11] Patent Number: 5,938,973
[45] Date of Patent: Aug. 17, 1999

[54] SWALLOW-TAILED COMPOUND AND FERRIELECTRIC LIQUID CRYSTAL COMPOSITION CONTAINING THE SAME

[75] Inventors: Yuki Motoyama; Tomoyuki Yui; Masahiro Johno; Takahiro Matsumoto, all of Tsukuba, Japan

[73] Assignee: Mitsubishi Gas Chemical Company, Tokyo, Japan

[21] Appl. No.: 08/927,795

[22] Filed: Sep. 11, 1997

[30] Foreign Application Priority Data

Sep. 13, 1996 [JP] Japan ................................ 8-243393

[51] Int. Cl.⁶ .................... C09K 19/12; C09K 19/20; C07C 69/76
[52] U.S. Cl. .................... 252/299.65; 252/299.67; 252/299.66; 560/65; 560/67; 560/73
[58] Field of Search ................ 252/299.65, 299.67, 252/299.66; 560/65, 67, 73

[56] References Cited

U.S. PATENT DOCUMENTS

| | | | |
|---|---|---|---|
| 5,534,190 | 7/1996 | Johno et al. | 252/299.65 |
| 5,660,762 | 8/1997 | Ito et al. | 252/299.67 |

FOREIGN PATENT DOCUMENTS

| | | |
|---|---|---|
| 0487093 | 5/1992 | European Pat. Off. . |
| 0718274 | 6/1996 | European Pat. Off. . |
| 19513258 | 10/1995 | Germany . |
| 5150257 | 6/1993 | Japan . |
| 5249502 | 9/1993 | Japan . |
| 6-95080 | 4/1994 | Japan . |

OTHER PUBLICATIONS

Booth, et al., "The Ferro–, Ferri–And Antiferro–electric Properties of a Series of Novel 2–or 3–substituted–alkyl 4'–(4–dodecyloxybiphenyl–4–carbonyloxy)–benzoate esters", Liquid Crystals, 1996, vol. 20, No. 6, pp. 815–823.

Heinemann, et al., "Competition Between Dipolar and Steric Interactions In Swallow–Tailed Compounds", Liquid Crystals, 1993, vol. 13, No. 3, pp. 373–380.

(List continued on next page.)

*Primary Examiner*—C. H. Kelly
*Attorney, Agent, or Firm*—Sherman and Shalloway

[57] ABSTRACT

A swallow-tailed compound of the following general formula (1),

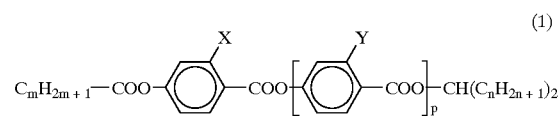

wherein m is an integer of 4 to 10, n is an integer of 2 to 6, p is 0 or 1 and each of X and Y is independently a hydrogen or fluorine atom; and a ferrielectric liquid crystal composition consisting essentially of the swallow-tailed compound of the general formula (1) and a ferrielectric liquid crystal compound of the following general formula (2),

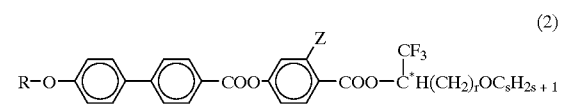

wherein R is a linear alkyl group having 6 to 12 carbon atoms, Z is a hydrogen or fluorine atom, r is an integer of 2 to 4 and s is an integer of 2 to 4. The ferrielectric liquid crystal composition has a ferrielectric phase in a broad temperature range and attains a fast response and a large tilt angle in a broad temperature range so that a ferrielectric liquid crystal display device having high display qualities can be provided.

6 Claims, 1 Drawing Sheet

OTHER PUBLICATIONS

Nito, et al., "TFT–driven Monstable Ferroelectric Liquid Crystal Display with Wide Viewing Angle and Fast Response Times", SIDS 1994 Preprint pp. 48–51.

Gorecka, et al. "Molecular Orientational Structures in Ferroelectric, Ferrielectric and Antiferroelectric Smectic Liquid Crystal Phases as Studied by Conoscope Observation", Jap. Journal of Appl. Physics, vol. 29, No. 1, Jan. 1990, pp. 131–137.

Nakagawa, M., "A Hysterisis Model for Antiferroelectric $SmC^*_A$ Phases", Jap. Journal of Appl. Physics, vol. 30, No 8, Aug. 1991, pp. 1759–1764.

Okabe, et al., "Reentrant Antiferroelectric Phase in 4–(1–Methylheptyloxy–carbonyl) phenyl–4'–Octylbiphenyl–4–Carboxylate", Jap. Journal of Appl. Physics, vol. 31 (1992), pp. L793–L796 (Part 2, No. 6B, Jun. 15, 1992).

Neubert et al., Mol. Crys. Liq. Crys., 1993, vol. 237 pp. 47–68. 1993.

SWALLOW-TAILED COMPOUND AND FERRIELECTRIC LIQUID CRYSTAL COMPOSITION CONTAINING THE SAME

FIELD OF THE INVENTION

The present invention relates to a novel swallow-tailed compound and a ferrielectric liquid crystal composition containing it. The composition is suitable for use in an active-matrix type liquid crystal display device in which each pixel is independently driven.

PRIOR ART

A liquid crystal display device (LCD) as a flat panel display has been superseding conventional Braun tube displays (CRT) mainly in the fields of portable machines and equipment. With the recent functional extension of personal computers and word processors and with the recent increase in the volume of data processing, LCD is also required to have higher functions such as a higher display capacity, full-color display, a wide viewing angle, a high-speed response and a higher contrast.

As a liquid crystal display method (liquid crystal driving method) to comply with the above requirements, there is proposed and practically used an active-matrix (AM) display device which works by a method in which thin film transistors (TFT) or diodes (MIM) are formed such that one transistor or diode corresponds to each pixel on a display screen and a liquid crystal is driven for each pixel independently of another.

The above display method has problems in that it is difficult to decrease a cost due to a low yield and that it is difficult to form a large display screen. Due to a high display quality, however, the above display method is about to surpass an STN display method which has been a conventional mainstream and to overtake CRT.

However, the above AM display device has the following problems due to the use of a TN (twisted nematic) liquid crystal compound as a liquid crystal material.

(1) A TN liquid crystal compound is a nematic liquid crystal, and the response speed is generally low (tens ms). In the video frame rate displays, no good display quality can be obtained.

(2) A twisted state (twist alignment) of liquid crystal molecules is used for displaying, and the viewing angle is therefore narrow. In a gray-scaling in particular, the viewing angle is sharply narrowed. That is, the contrast ratio and the color change depending upon viewing angles to a display screen.

For overcoming the above problems, in recent years, there have been proposed AM panels which use a ferroelectric liquid crystal compound or an anti-ferroelectric liquid crystal compound in place of the TN liquid crystal compound (see Japanese Laid-open Patent Publications Nos. 249502/1993, 150257/1993 and 95080/1994). However, the following problems remain to solve for practical use of these liquid crystal compounds.

(A) A ferroelectric liquid crystal has spontaneous polarization. An image sticking on the display screen is liable to take place due to constant spontaneous polarization and hence, the driving becomes difficult.

In a display with a ferroelectric liquid crystal compound in a surface-stabilized mode, it is very difficult to perform a gray-scaling since only a bistate of black and white is possible to display in principle. For a gray-scaling, a special devising is required (e.g., ferroelectric liquid crystal device using monostability; Keiichi NITO et al., SID '94, Preprint, p. 48), and it is required to develop a very high technique for practical use.

(B) An anti-ferroelectric liquid crystal compound is free of the image sticking problem described in the above (1) since it has no permanent spontaneous polarization.

The AM driving requires a liquid crystal material which can be at least driven at 10 V or less. However, the anti-ferroelectric liquid crystal generally shows a high threshold voltage, and its driving at a low voltage is therefore difficult. Further, it has a problem that a gray-scaling is difficult to perform since its optical response involves a hysteresis.

It is an object of the present invention to provide a new material which can overcome the above problems and suitably used in AM driving, and a liquid crystal compound having a ferrielectric phase may be expectable as the above novel material.

A ferrielectric liquid crystal compound having a ferrielectric phase (SCγ* phase) was found for the first time in 4-(1-methylheptyloxycarbonyl)phenyl=4-(4'-octyloxybiphenyl)carboxylate (called "MHPOBC" for short) in 1989 (Japanese Journal of Applied Physics, Vol. 29, No. 1, 1990, pp. L131–137).

The structural formula and phase transition temperatures of the MHPOBC are as follows.

Structure formula:

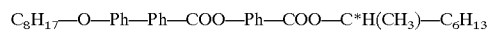

$C_8H_{17}$—O—Ph—Ph—COO—Ph—COO—$C^*H(CH_3)$—$C_6H_{13}$ wherein Ph is a 1,4-phenylne group and C* is an asymmetric carbon atom.

Phase sequence:

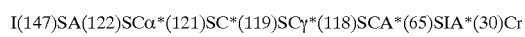

I(147)SA(122)SCα*(121)SC*(119)SCγ*(118)SCA*(65)SIA*(30)Cr wherein I is an isotropic phase, SA is a smectic A phase, SCα* is a chiral smectic Cα phase, SC* is a chiral smectic C phase (ferroelectric phase), SCγ* is a chiral smectic Cγ phase (ferrielectric phase), SCA* is a chiral smetic CA phase (anti-ferroelectric phase), SIA* is a chiral smectic IA phase, and Cr is a crystal phase.

BRIEF DESCRIPTION OF DRAWINGS

For explaining a ferrielectric liquid crystal compound, FIG. 1 shows molecular arrangement states of a ferrielectric phase, and FIG. 2 shows an optical response of a ferrielectric phase to a triangular wave.

Figure 1:
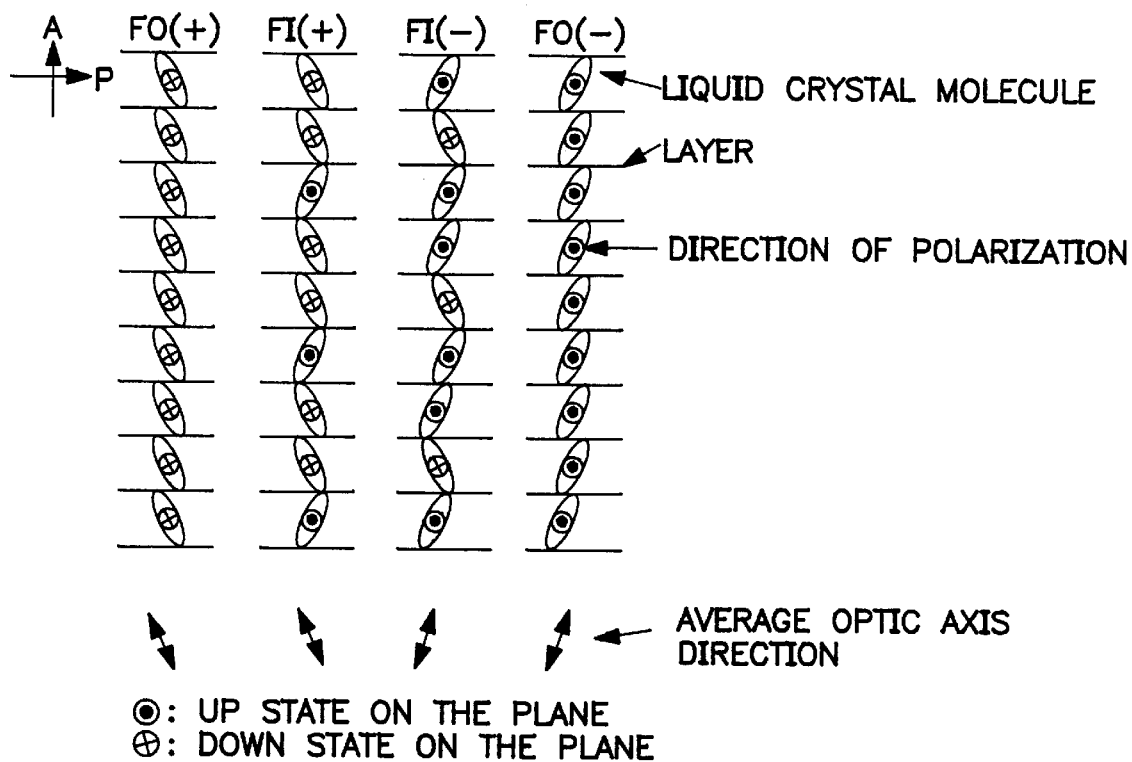
FIG. 1 shows a molecular arrangement state of a ferrielectric phase. FI(+) and FI(−) show a ferrielectric state, and FO(+) and FO(−) show an anti-ferroelectric state.

A ferrielectric phase has a molecular arrangement of FI(+) (a case where a charged voltage is positive) or a molecular arrangement state of FI(−) (a case where a charged voltage is negative) as shown in FIG. 1. In a state free of an electric field, FI(+) and FI(−) are equivalent and are therefore co-present.

Therefore, average optic axes are in the direction of a layer normal, and the state free from an electric field is in a dark state under the condition of a polarizer shown in FIG. 1. This state corresponds to a portion showing a voltage of 0 and a transmission of 0 in FIG. 2.

Further, each of FI(+) and FI(−) has spontaneous polarization as is clearly shown by the molecular arrangement states, while the spontaneous polarizations are cancelled in a state in which these are co-present. As a result, an average spontaneous polarization is zero. Thus, a ferrielectric liquid crystal compound is free from an image sticking phenomenon occurred in a ferroelectric liquid crystal compound, similarly to an anti-ferroelectric liquid crystal compound.

When a voltage applied to a ferrielectric liquid crystal compound is increased, a region (domain) having an extinguished position appears at a voltage before a ferroelectric phase is reached. This shows that the above domain has an optic axis in the direction which tilts from the direction of layer normal although the tilt is not so large as that in a ferroelectric state.

Figure 2:
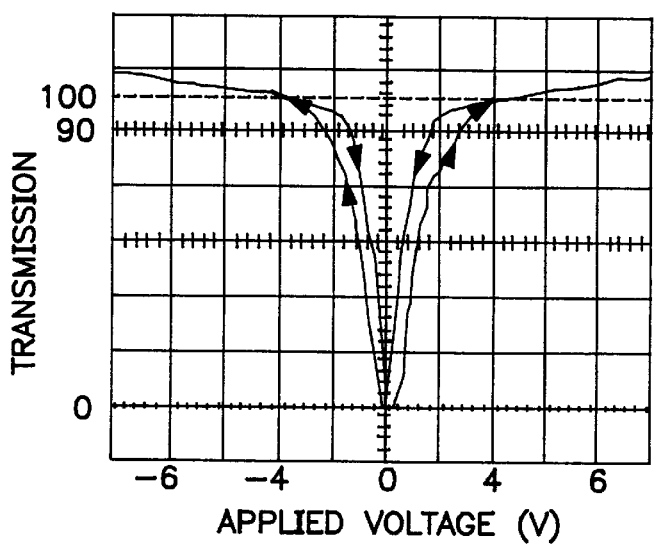
FIG. 2 shows an optical response of a ferrielectric phase to a triangular wave voltage.

This intermediate state is considered FI(+) or FI(−). In this case, a change in transmission is to be observed between voltages of 0 V and 4 V in FIG. 2 not as a continuous change but as a stepwise change. However, a continuous change in transmission is observed as shown in FIG. 2. This is presumably because the threshold voltage in a change from FI(+) to FO(+) or from FI(−) to FO(−) is not distinct.

In the present invention, a liquid crystal phase which necessarily shows the above-explained intermediate state is called a ferrielectric phase, and a liquid crystal compound of which the ferrielectric phase is the broadest in the phase sequence is called a ferrielectric liquid crystal compound.

When the charged voltage is further increased, the ferrielectric phase undergoes a phase transition to a stable ferroelectric phase FO(+) or FO(−) depending upon a direction of the electric field. That is, a portion in which the transmission is brought into a saturated state (flat portions on left and right sides) in FIG. 2 is FO(+) or FO(−).

In the above ferroelectric state FO(+) or FO(−), a spontaneous polarization greater than that in the ferrielectric phase FI(+) or FI(−) is exhibited as is seen in FIG. 1.

As explained above, in the ferrielectric phase, a state where FI(+) and FI(−) are co-present is used as dark, and ferroelectric states FO(+) and FO(−) are used as light.

A conventional ferroelectric liquid crystal compound provides a switching between FO(+) and FO(−), while the ferrielectric phase has a great characteristic feature in switching among four states of FO(+), FI(+), FI(−) and FO(−).

These display principles based on the ferrielectric liquid crystal compound use birefringence of a liquid crystal, and when the ferrielectric phase is used, a display device having a wide viewing angle can be produced.

As shown in FIG. 2, in the ferrielectric phase, a difference between the voltage required for a change from a ferrielectric state to a ferroelectric state and the voltage required for a change from a ferroelectric state to a ferrielectric state is generally small. That is, the ferrielectric phase highly tends to have a narrow width of hysteresis and characteristically shows a V-letter-shaped optical response, and the ferrielectric phase therefore has characteristics suitable for AM driving and a gray-scaling in AM driving.

Further, in changes of the ferrielectric liquid crystal compound depending upon voltages, the threshold voltage which is a voltage required for a change from a ferrielectric state to a ferroelectric state tends to be far low as compared with an anti-ferroelectric liquid crystal compound, and it can be also said from this point that the ferrielectric liquid crystal compound is suitable for AM driving.

Generally, the driving voltage for an AM driven device is low, and the AM driven device is at least required to be driven at a high speed at a charged voltage of not more than 10 V. In respect of this point, conventional liquid crystals having a ferrielectric phase have a problem on the response at a driving voltage of not more than 10 V, and an improvement in this respect is strongly desired.

Generally, the ferrielectric liquid crystal compound can be driven at a voltage of not more than 10 V, since the voltage for its transition from a ferrielectric state to a ferroelectric phase is very low. Since, however, the ferrielectric liquid crystal compound has a very large rotation viscosity, a sufficient response performance cannot be obtained in some cases.

For improving the ferrielectric liquid crystal compound in the above point, conventionally, a compound having a viscosity-decreasing effect has been added. For attaining a response performance satisfactory to some extent, it was necessary to add a considerable amount of a viscosity-decreasing agent. As a result, there was caused a problem in that the upper transition temperature of the ferrielectric phase decreases or that the tilt angle decreases. It has been therefore difficult to obtain a practically satisfactory composition. In particular, a decrease in the tilt angle decreases the brightness of a display device, and there is therefore a serious problem in that the contrast decreases.

The present invention has been made from the above viewpoint, and it is to provide a swallow-tailed compound which has a viscosity-decreasing effect and has an effect on improving the response performance without much decreasing the tilt angle when added to a ferrielectric liquid crystal compound, and to provide also a ferrielectric liquid crystal composition containing the above compound, which composition is suitable for use by AM driving.

For putting a ferrielectric liquid crystal compound to practical use, it is required to improve its response performance without decreasing its tilt angle. According to M. Nakagawa, the response speed of an anti-ferroelectric liquid crystal depends upon the rotation viscosity of liquid crystal molecules (Masahiro Nakagawa, Japanese Journal of Applied Physics, 30, 1759 (1991)). That is, with a decrease in viscosity, the response speed increases.

Further, when the response speed relative to temperature is observed, the response speed starts to become slow around room temperature and exponential-functionally becomes slow in the temperature range lower than room temperature. An anti-ferroelectric liquid crystal compound has a high viscosity since its liquid crystal phase is a smectic phase, so that its viscosity sharply increases on a low-temperature side, and it is considered that the response speed sharply decreases due to the viscosity resistance thereof. The ferrielectric liquid crystal compound presumably causes entirely the same phenomenon.

It is one specific thinkable method for overcoming the above problem to make an attempt to add a compound having a relatively low viscosity to a liquid crystal composition in order to decrease the viscosity of the composition as a whole thereby to improve the response speed. This method is considered the most practical solution at present, but it is anticipated that it not only tends to drop the upper transition temperature of the ferrielectric phase, but also decreases the tilt angle of the liquid crystal.

In the case of a ferrielectric liquid crystal display device for a display, it is generally considered that the temperature of the device increases up to about 40° C. due to the heat of backlight. For normal driving of the device, therefore, the upper transition temperature of the ferrielectric phase is required to be at least 40° C., preferably at least 50° C.

For obtaining a good alignment, a smectic A phase is required to exist on the high temperature side of the ferrielectric phase. Further, on the lower transition temperature side, the device is at least required to be driven at 10° C., and therefore, the lower transition temperature of the ferrielectric phase is at least required to be 0° C.

Further, as the tilt angle decreases, the luminance decreases and the brightness of the device decreases. The product quality of the device therefore decreases even if the response speed is improved, and there is therefore required an additive which does not decrease the tilt angle.

The present invention has been made from the above viewpoint, and it has been found that when a specific novel swallow-tailed compound is selected and mixed with a specific ferrielectric liquid crystal compound, there can be obtained a ferrielectric liquid crystal composition which is improved in the response speed without causing a decrease in the upper transition temperature of the ferrielectric phase and without causing a decrease in the tilt angle. The present invention has been accordingly completed.

According to the present invention, there is provided a novel swallow-tailed compound of the following general formula (1),

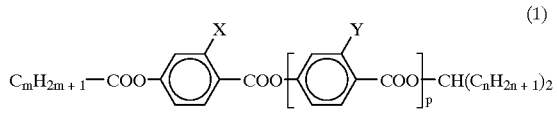

wherein m is an integer of 4 to 10, n is an integer of 2 to 6, p is 0 or 1 and each of X and Y is independently a hydrogen or fluorine atom.

According to the present invention, further, there is provided a ferrielectric liquid crystal composition consisting essentially of the swallow-tailed compound of the above general formula (1) and a ferrielectric liquid crystal compound of the following general formula (2),

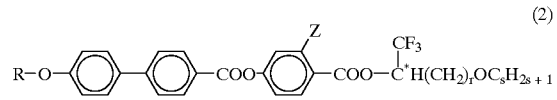

wherein R is a linear alkyl group having 6 to 12 carbon atoms, Z is a hydrogen or fluorine atom, r is an integer of 2 to 4, s is an integer of 2 to 4 and C* is an asymmetric carbon atom.

The preferred swallow-tailed compound has the above general formula (1) in which m is an integer of 4 to 9 and n is an integer of 2 to 5 and has no liquid crystal phase.

The ferrielectric liquid crystal composition of the present invention consists essentially of the swallow-tailed compound of the above general formula (1) and the ferrielectric liquid crystal compound of the above general formula (2). The ferrielectric liquid crystal composition of the present invention contains 1 to 40 mol % of the former compound and 99 to 60 mol % of the latter compound, preferably 2 to 35 mol % of the former compound and 98 to 65 mol % of the latter compound.

In the ferrielectric liquid crystal composition of the present invention, preferably, the ferrielectric phase has a phase transition temperature on the high temperature side of 40° C. or higher and the phase transition temperature on the low temperature side of 0° C. or lower, and has a smectic A phase that is exhibited on the higher temperature side than a temperature at which the ferrielectric phase is exhibited.

The ferrielectric liquid crystal composition of the present invention is sandwiched between substrates provided with non-linear active devices such as thin-film transistors or diodes for each of pixels, and the resultant device is preferably used as an active-matrix liquid crystal display device. In the liquid crystal display device with the non-linear active devices, the driving of the liquid crystal by voltage is performed by switching among two ferrielectric phases, two ferroelectric phases and intermediate states therebetween.

The ferrielectric liquid crystal compound of the present invention can be easily produced, for example, by the following reaction scheme.

(1) AcO—Ph(F)—COOH+SOCl$_2$→AcO—Ph(F)—COCl (2) (1)+CF$_3$C*H(OH) (CH$_2$)$_r$OC$_s$H$_{2s+1}$→AcO—Ph(F)—COO—C*H(CF$_3$)(CH$_2$)$_r$OC$_s$H$_{2s+1}$ (3) (2)+(Ph—CH$_2$NH$_2$)→HO—Ph(F)—COO—C*H(CF$_3$)(CH$_2$)$_r$OC$_s$H$_{2s+1}$ (4) R—O—Ph—Ph—COOH+SOCl$_2$→R—O—Ph—Ph—COCl (5) (3)+(4)→ferrielectric liquid crystal compound as an end product.

In the above formulae, AcO is an acetyl group, Ph is a 1,4-phenylene group, Ph(F) is a 1,4-phenylene group on the 3-position of which –F is substituted, and R, r, s and C* are as defined in the above general formula (2).

The above production scheme will be briefly explained below.

(1) shows the chlorination of fluorine-substituted or non-substituted p-acetoxybenzoic acid with thionyl chloride.

(2) shows the formation of an ester by a reaction between the chloride (1) and an optically active alcohol.

(3) shows the deacetylation of the ester (2).

(4) shows the chlorination of 4'-alkyloxybiphenyl-4-carboxylic acid.

(5) shows the production of the liquid crystal compound by a reaction between the phenol (3) and the chloride (4).

As described above, the present invention provides a novel swallow-tailed compound and a ferrielectric liquid crystal composition containing it. The ferrielectric liquid crystal composition provided by the present invention has a ferrielectric phase in a broad temperature range and performs a high response speed in a broad temperature range. Further, the composition has a large tilt angle. There can be therefore provided a ferrielectric liquid crystal display device having high display qualities.

EXAMPLES

The present invention will be further specifically explained with reference to Examples and Comparative Examples hereinafter, while the present invention shall not be limited thereto.

Example 1

Preparation of 3-fluoro-4-(1-ethylpropyloxycarbonyl)phenyl=4-n-decanoyloxybenzoate (general formula (1): m=9, n=2, p=1, X=H, Y=F (E1)):
(1) Preparation of 4-decanoyloxybenzoic acid 13.8 Grams (0.1 mol) of 4-hydroxybenzoic acid was dissolved in 140 ml of dichloromethane. To this mixture were consecutively added 16 ml of triethylamine, 20.1 g (0.11 mol) of n-decanoic acid chloride and 0.97 g (0.0079 mol) dimethylaminopyridine, and the mixture was stirred at room temperature over 1 day and night. To this reaction mixture was added 50 ml of 10% hydrochloric acid, and the mixture was extracted with 100 ml of ether three times. An organic layer was washed with 100 ml of sodium chloride aqueous solution three times, and dried over anhydrous sodium sulfate. The solvent was distilled off, and the residue was washed with 400 ml of hexane to give 25.5 g (yield 82%) of 4-decanoyloxybenzoic acid as an end product.

(2) Preparation of 4-acetoxy-2-fluoro-1-(1-ethylpropyloxycabonyl)benzene

Thionyl chloride in an amount of 60 ml was added to 11.9 g (0.06 mol) of 4-acetoxy-2-fluorobenzoic acid, and the mixture was allowed to react under reflux for 7 hours. Then, excessive thionyl chloride was distilled off, and then 10 ml of pyridine and 3.5 g (0.0420 mol) of 3-pentanol were dropwise added. After the dropwise addition, the mixture was stirred at room temperature over 1 day and night, and then diluted with 200 ml of ether. An organic layer was consecutively washed with diluted hydrochloric acid, with a 1N sodium hydroxide aqueous solution and with water, and dried over magnesium sulfate. The solvent was distilled off, and the resultant crude end product was purified by silica gel column chromatography using hexane/ethyl acetate as a solvent to give 10.7 g (yield 90%) of the end product.

(3) Preparation of 4-hydroxy-2-fluoro-1-(1-ethylpropyloxycarbonyl)benzene 10.3 Grams (0.0361 mol) of the compound obtained in (2) was dissolved in 250 ml of ethanol, and 7.74 g (0.0772 mol) of benzylamine was dropwise added. Further, the mixture was stirred at room temperature over 1 day and night and then diluted with 300 ml of ether. The diluted solution was consecutively washed with diluted hydrochloric acid and with water, and dried over magnesium sulfate. The solvent was distilled off, and the residue was isolated and purified by silica gel column chromatography to give 8.5 g (yield 98%) of the end product.

(4) Preparation of 3-fluoro-4-(1-ethylpropyloxycarbonyl) phenyl-4-n-decanoyloxybenzoate Thionyl chloride in an amount of 15 ml was added to 3.1 mmol of the compound obtained in the above (1), and the mixture was refluxed under heating for 5 hours. Excessive thionyl chloride was distilled off, then, 2 ml of pyridine and 2.12 mmol of the compound obtained in the above (3) were added, and the mixture was allowed to react at room temperature for 10 hours.

After termination of the reaction, the reaction mixture was diluted with 300 ml of ether, and consecutively washed with diluted hydrochloric acid, with a 1N sodium carbonate aqueous solution and with water. An organic layer was dried over magnesium sulfate. Then, the solvent was distilled off, and silica gel column chromatography is used for isolation to give 0.95 g (yield 87%) of the end product.

Examples 2 and 3

Preparation of 4-(1-propylbutyloxycarbonyl)phenyl=2-fluoro-4-decanoyloxybenzoate (general formula (1): m=9, n=3, p=1, X=F, Y=H (E2)) and 3-fluoro-4-(1-butylpentyloxycarbonyl)phenyl=4-n-decanoyloxybenzoate (general formula (1): m=9, n=4, p=1, X=H, Y=F (E3)):

End products were obtained in the same manner as in Example 1 except that the 3-pentanol was replaced with 4-heptanol and 4-hydroxybenzoic acid was replaced with 4-hydroxy-2-fluorobenzoic acid(Example 2) or the 3-pentanol was replaced with 5-nonanol (Example 3).

Example 4

Preparation of 4-(1-propylbutyloxycarbonyl)phenyl=4-decanoyloxybenzoate (general formula (1): m=9, n=3, p=1, X=H, Y=H (E4)):

An end product was obtained in the same manner as in Example 1 except that the 4-acetoxy-2-fluorobenzoic acid was replaced with 4-acetoxybenzoic acid.

Example 5

Preparation of 3-fluoro-4-n-hexanoyloxy-1-(1-propylbutyl)benzoate (general formula (1): m=5, n=3, p=0, X=F (E5)):

An end product was obtained by reacting heptanol according to Example 1 except that the 4-decanoyloxybenzoic acid was replaced with 2-fluoro-4-hexanoyloxybenzoic acid.

Table 1 shows $^1$H-NMR data and melting points of the end compounds (E1 to E5) obtained in Examples 1 to 5, and their chemical formulae are shown by (E1) to (E5). Further, as a result of texture observation and measurement of DSC (differential scanning calorimeter) of these compounds, no liquid crystal phase was observed in these compounds.

TABLE 1

| Proton No. | 1 | 2 | 3 | 4 | 5 | 6 | 7 | Melting point (°C.) |
|---|---|---|---|---|---|---|---|---|
| Example 1 | 2.6 | 7.2 | 8.2 | 7.1 | 7.2 | 8.0 | 5.0 | 32 |
| Example 2 | 2.6 | 7.1 | 7.0 | 8.2 | 7.3 | 8.2 | 5.2 | −21 |
| Example 3 | 2.6 | 7.3 | 8.2 | 7.1 | 7.1 | 8.0 | 5.2 | 11 |
| Example 4 | 2.6 | 7.3 | 8.2 | 7.1 | 7.1 | 8.0 | 5.2 | 14 |
| Example 5 | 2.6 | 7.0 | 7.0 | 8.0 | 5.2 |  |  | <−60 |

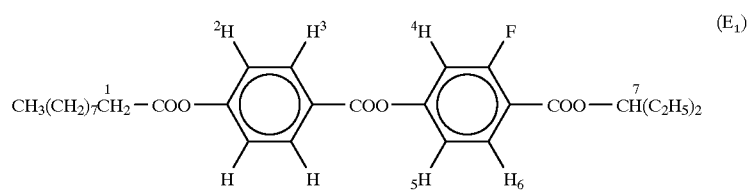

TABLE 1-continued

| Proton No. | 1 | 2 | 3 | 4 | 5 | 6 | 7 | Melting point (°C.) |
|---|---|---|---|---|---|---|---|---|

[Structure $(E_2)$: CH$_3$(CH$_2$)$_7$$^1$CH$_2$—COO—[phenyl with $^2$H, F, $_3$H, H$_4$]—COO—[phenyl with $^5$H, H$^6$, H, H]—COO—$^7$CH(C$_3$H$_7$)$_2$]

[Structure $(E_3)$: CH$_3$(CH$_2$)$_7$$^1$CH$_2$—COO—[phenyl with $^2$H, H$^3$, H, H]—COO—[phenyl with $^4$H, F, $_5$H, H$_6$]—COO—$^7$CH(C$_4$H$_9$)$_2$]

[Structure $(E_4)$: CH$_3$(CH$_2$)$_7$$^1$CH$_2$—COO—[phenyl with $^2$H, H$^3$, H, H]—COO—[phenyl with $^4$H, H$^5$, H, H]—COO—$^6$CH(C$_3$H$_7$)$_2$]

[Structure $(E_6)$: CH$_3$(CH$_2$)$_3$$^1$CH$_2$—COO—[phenyl with $^2$H, F, $_3$H, H$_4$]—COO—$^5$CH(C$_3$H$_7$)$_2$]

Example 6

20 Mol % of the swallow-tailed compound (E2) obtained in Example 2 was added to a ferrielectric liquid crystal compound (2A) having the following formula, to obtain a ferrielectric liquid crystal composition.

The ferrielectric liquid crystal composition was measured for a phase sequence, a tilt angle and a response speed, and Table 2 shows the results.

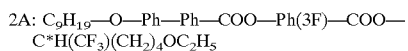

2A: C$_9$H$_{19}$—O—Ph—Ph—COO—Ph(3F)—COO—C*H(CF$_3$)(CH$_2$)$_4$OC$_2$H$_5$ in which Ph is a 1,4-phenylene group, Ph(3F) is a 1,4-phenylene group on the 3-position of which fluorine is substituted, and C* is an asymmetric carbon atom.

The ferrielectric liquid crystal composition was identified for liquid crystal phases by texture observation, conoscopic image observation and DSC (differential scanning calorimeter) measurement. The observation of a conoscopic image is effective means of identifying a ferrielectric phase. The conoscopic image observation was conducted according to literature (J. Appl. Phys. 31, 793 (1992)).

The ferrielectric liquid crystal composition was measured for a response speed, etc., by the following methods.

A pair of glass plates with insulation layer (SiO$_2$, thickness; 50 nm) and ITO electrodes were coated with polyimide (thickness; about 80 nm), and one of the glass plates was rubbed. The glass plates were attached to each other through a spacer having a particle diameter of 1.6 μm to form a test cell. The cell had a thickness of 2 μm. The liquid crystal composition was heated until the liquid crystal showed an isotropic phase, and the composition was charged into the test cell by capillarity. Then, the cell was gradually cooled at a rate of 1° C./minute to align the liquid crystal in parallel.

Then, the test cell was driven by applying ±10 V triangular wave voltage having a frequency of 10 Hz to the test cell at a predetermined temperature, to measure a tilt angle.

Further, the time required for a change in the transmission by 90% under the application of 8 V pulse voltage having a frequency of 10 Hz was defined as a response time, and the response time was measured.

TABLE 2

| | Phase sequence | Tilt angle (°) | Response time (μs) | Measurement temperature (° C.) |
|---|---|---|---|---|
| Ex. 6 | Cr(<−10)SCγ*(64)SA(72)I | 32 | 37 | 30 |
| Liquid crystal | Cr(<−0)SCγ*(89)SA(91)I | 34 | 80 | 30 |

Ex. = Example

In the above phase sequences, parenthesized values are transition temperatures (°C.), Cr is a crystal phase, SCγ* is a chiral smectic Cγ phase (ferrielectric phase), SA is a smectic A phase and I is an isotropic phase.

What is claimed is:
1. A ferrielectric liquid crystal composition consisting essentially of a swallow-tailed compound of the general formula (1),

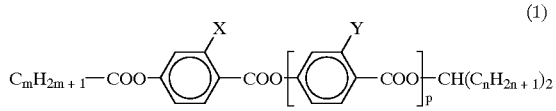

(1)

wherein m is an integer of 4 to 10, n is an integer of 2 to 6, p is 0 or 1 and each of X and Y is independently a hydrogen or fluorine atom, and a ferrielectric liquid crystal compound of the general formula (2),

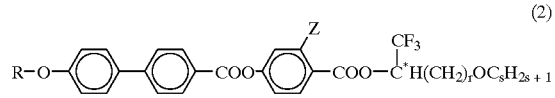

(2)

wherein R is a linear alkyl group having 6 to 12 carbon atoms, Z is a hydrogen or fluorine atom, r is an integer of 2 to 4, s is an integer of 2 to 4 and C* is an asymmetric carbon atom.

2. The composition of claim 1, wherein the composition contains 1 to 40 mol % of the swallow-tailed compound of the general formula (1) and 99 to 60 mol % of the ferrielectric liquid crystal compound of the general formula (2).

3. The composition of claim 1, wherein the composition contains the compound of the general formula (1) in which m is an integer of 4 to 9 and n is an integer of 2 to 5.

4. The composition of claim 1, wherein the ferrielectric phase has a phase transition temperature of 40° C. or higher, a phase transition temperature of 0° C. or lower, and has a smectic A phase at a higher temperature than the ferrielectric phase.

5. An active matrix liquid crystal display device obtained by sandwiching the ferrielectric liquid crystal composition recited in claim 1 between substrates provided with non-linear active elements of thin-film transistors or diodes for each of pixels.

6. The device of claim 5, wherein application of different voltages to the liquid crystal composition using non-linear active elements causes switching among two ferrielectric phases, two ferroelectric phases and intermediate states therebetween.

* * * * *